United States Patent [19]
Coe

[11] Patent Number: 6,102,871
[45] Date of Patent: Aug. 15, 2000

[54] BLOOD COLLECTION FUNNEL

[76] Inventor: Rosemarie O. Coe, 1614 Maple Cir., Parkersburg, W. Va. 26101

[21] Appl. No.: 09/197,439

[22] Filed: Nov. 23, 1998

[51] Int. Cl.$^7$ ........................................................ A61B 5/00
[52] U.S. Cl. ........................................... 600/575; 604/317
[58] Field of Search ..................................... 600/573, 575, 600/583; 604/317, 318, 403; 222/478, 485, 566, 575

[56] References Cited

U.S. PATENT DOCUMENTS

| | | |
|---|---|---|
| 639,486 | 12/1899 | Wright . |
| 1,267,658 | 5/1918 | Green . |
| 3,187,750 | 6/1965 | Tenczar, Jr. . |
| 3,199,507 | 8/1965 | Kamm . |
| 3,604,410 | 9/1971 | Whitacre ................................. 600/575 |
| 3,606,103 | 9/1971 | Taylor . |
| 3,635,091 | 1/1972 | Linzer et al. . |
| 3,922,913 | 12/1975 | Scott ...................................... 600/575 |
| 4,335,730 | 6/1982 | Griffin . |
| 4,879,098 | 11/1989 | Oberhardt et al. ....................... 600/573 |
| 5,342,328 | 8/1994 | Grossman et al. . |
| 5,388,699 | 2/1995 | Ratajczak et al. ...................... 600/573 |
| 5,423,792 | 6/1995 | Oxley . |
| 5,569,225 | 10/1996 | Fleury . |
| 5,667,485 | 9/1997 | Lindsay . |

FOREIGN PATENT DOCUMENTS

| | | |
|---|---|---|
| 2552653 | 4/1985 | France . |
| 3420855 | 12/1985 | Germany . |
| 3439420 | 4/1986 | Germany . |
| 91/16086 | 10/1991 | WIPO . |

*Primary Examiner*—Max Hindenburg
*Attorney, Agent, or Firm*—Robert N. Blackmon

[57] ABSTRACT

A method and apparatus for reliably collecting blood from the umbilical cord of a newborn infant having a funnel having multiple spouts for simultaneously filling a plurality of test tubes. A funnel having a number of spouts on its lower end below a central, tapered receiving chamber is provided to collect blood from an umbilical cord or other blood source held over the wide mouthed funnel. A number of test tubes for transporting the blood to various labs or testing facilities are insertable over the ends of the spouts below the funnel to easily and directly pour the blood from the umbilical cord through the funnel to the test tubes. The spouts may have a tapered surface, an elastomeric surface, or appropriately sized to securely receive the test tubes.

11 Claims, 2 Drawing Sheets

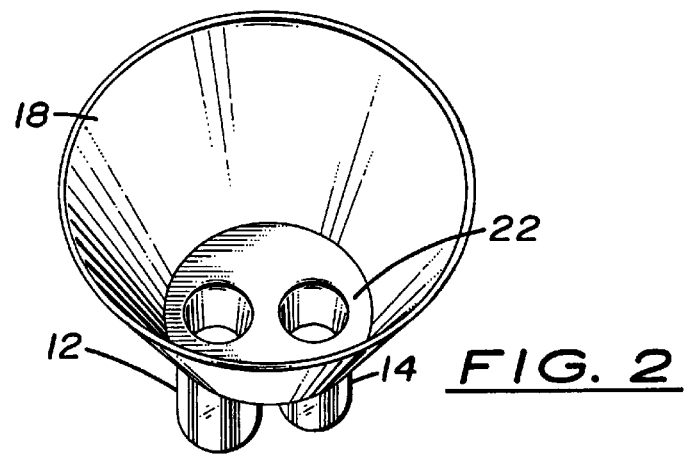
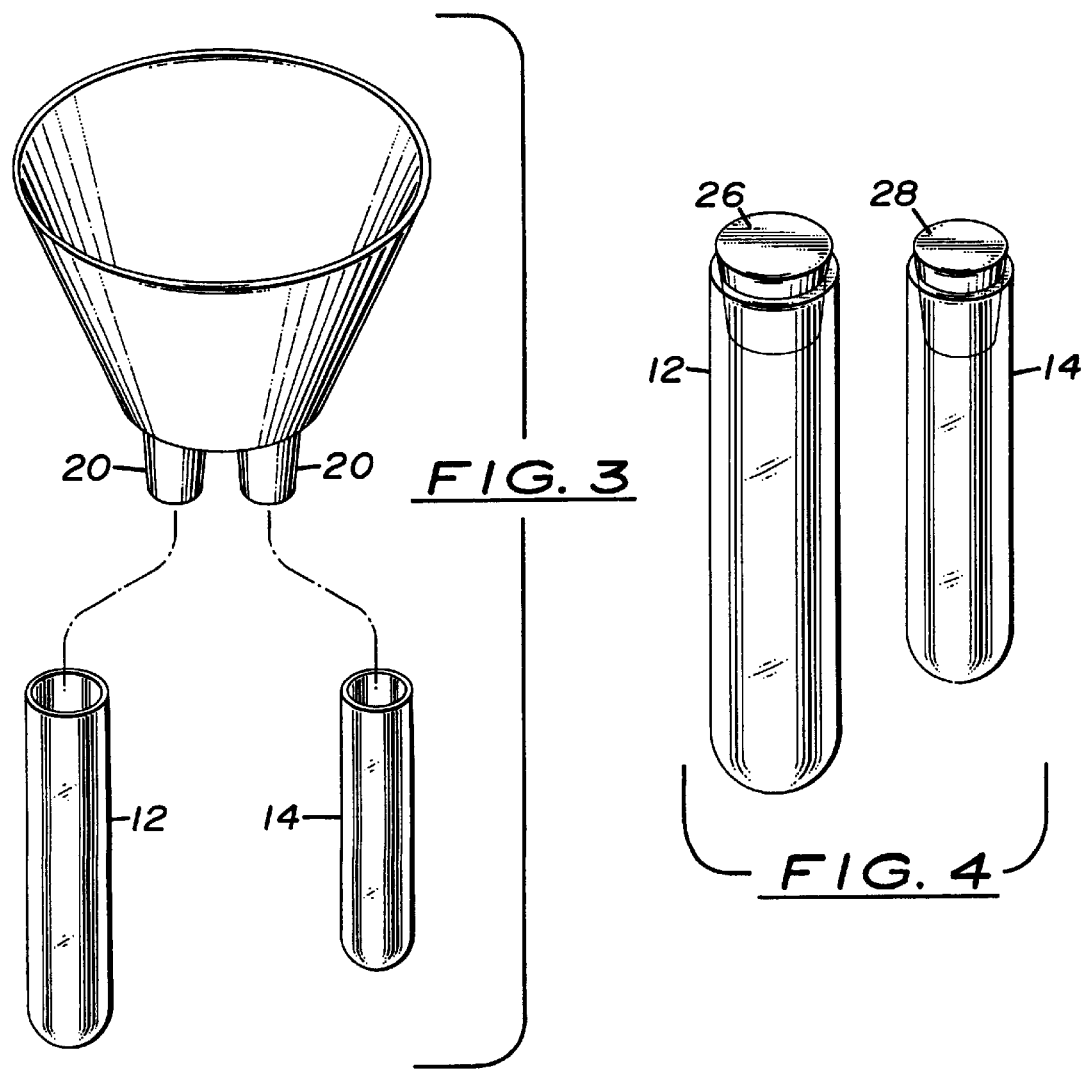

BLOOD COLLECTION FUNNEL

BACKGROUND OF THE INVENTION

1. Field of the Invention

The present invention relates to an improved method of collecting blood of a newborn during delivery including a disposable, blood collection funnel for receiving umbilical cord blood and having multiple lower spouts for transferring collected blood to a plurality of blood collection tubes which may be used for further testing.

2. Description of the Prior Art

Immediately following the delivery of a newborn, it is essential to collect blood samples for laboratory analysis of the blood type, RH factor, and blood count of the newborn. In addition, other tests are needed to test blood clotting for additional cord bilirubin present, and if any particular medical concerns are present, blood may have to be tested for other specific problems as well.

Presently cord blood is collected with a glass beaker or drawn with a syringe. After the umbilical cord is cut and clamped. The doctor holds the cord over a medicine glass and unclamps one end of the cord to collect the blood. Pouring the blood from the cord into the medicine glass in this manner can be a difficult process, especially after the doctor or staff has just completed the delivery of a child after a prolonged labor. Spillage from the process is not uncommon and the container typically will have blood on the outside, increasing the possibility of blood contamination and increasing the likelihood of exposure of the hospital staff to the potentially infected blood, which is of primary concern to medical staff.

Another method used by doctors is to use a syringe and draw it out of a vein in the cord directly and plunging the blood into the medicine glass or appropriate container or collection tubes. One difficulty with this process is that the blood may become hemolyzed during this procedure. Also the unnecessary use of a syringe increases the possibility of accidental sticking a staff member with the syringe filled with blood. In addition, the use of a syringe for this process increases the amount of medical waste produced and increases the amount of time required for post birthing procedures thereby increasing the cost to the patient and insurers.

After the blood has been collected and placed into the medicine glass, it is then passed on to a scrub nurse and set on the instrument table for the circulating nurse to pour into blood collecting tubes. The tubes are color coordinated with a red top and purple top. The red top tube is used for blood typing and blood counting. The tube with the purple top is used for cord bilirubin tests.

All of this is occurring a very crucial time of delivery. After the umbilical cord has been cut, the infant is handed to the circulating curse to stabilize the infant. If the infant is not doing well, she is tied up taking care of the infant and the cord blood clots, as the blood clots very quickly if not handled immediately. Once the blood clots it is no longer satisfactory for the precise tests needed. Without the cord blood, then a blood specimen must to be taken after the delivery is finished from a vein in the placenta with a syringe. Most of the time this is not successful and it can be very messy and time consuming. If the specimen can't be obtained or a good specimen or not enough then the infant has to be suck for a specimen. This is of course disadvantageous for obvious reasons and dangers.

Additionally, if the container is bloody and the nurse didn't have time to don a pair of gloves then there is a chance of blood contamination or exposure. When the nurse pours the blood into the blood collecting tubes it may spill all over the tube resulting in blood contamination and further exposure to the nurse.

One such attempt to facilitate the collection of umbilical cord blood is U.S. Pat. No. 5,342,328 issued Aug. 30, 1994 to Grossman et al., which shows a container having an upper, closable container for receiving a clamped section of umbilical cord. The main chamber has an funnel portion for draining the blood from the unclamped cord into a tube which can be placed below and in communication with the chamber.

Published International Patent Application WO 91/16086 published Oct. 31, 1991 to Target Research Company shows a multi-compartment biological fluid specimen bag for collecting urine and other biological specimens for drug testing or other controlled substances.

None of the above inventions and patents, taken either singly or in combination, is seen to describe the instant invention as claimed.

SUMMARY OF THE INVENTION

The present invention minimizes the possibility of blood contamination and exposure of the blood to the medical staff by providing a convenient blood collection funnel which may be attached to a plurality of test tubes for the simple and convenient collection of blood. The blood collection funnel may have at its upper end a wide mouth for receiving the flow of blood from a umbilical cord or other container of blood and a plurality of lower spouts for directing the flow of blood into a plurality of test tubes or other containers. The test tubes may have chemicals, such as anticoagulants or other agents in various of the tubes to facilitate preparation and preservation of the samples for further tests. The spouts may all be of a similar size or may be sized to receive tubes and containers of different diameter openings.

Accordingly, it is a principal object of the invention to provide an improved, disposable blood collection funnel for facilitating the collection of blood during delivery and post-delivery procedures.

It is another object of the invention to provide a funnel having a wide mouth for allowing spill-free pouring of blood from an umbilical cord into the inner, receiving chamber of the funnel for collection of the blood.

It is a further object of the invention to provide a blood collection funnel having a plurality of directing spouts attached and in communication with the inner, receiving chamber of the funnel for directing the flow of the blood out of the chamber.

Still another object of the invention is to provide a plurality of directing spouts on a blood collection funnel for receiving the upper ends of test tubes for directing flow from the funnel to a plurality of test tubes which can be used for transporting and testing of the blood.

Still a further object of the invention is to provide a blood collection kit which includes a blood collection funnel and a plurality of test tubes for collecting blood, wherein the test tubes may also include chemicals for protecting and preserving the blood samples which are to be tested.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 2 is a perspective view of the blood collection funnel from above with no test tubes attached to the funnel.

FIG. 3 is an environmental view of the funnel showing the interrelation of the funnel and the test tubes.

FIG. 4 is a perspective view of the test tubes with color coordinated caps.

Similar reference characters denote corresponding features consistently throughout the attached drawings.

DETAILED DESCRIPTION OF THE PREFERRED EMBODIMENT(S)

Figure 1:
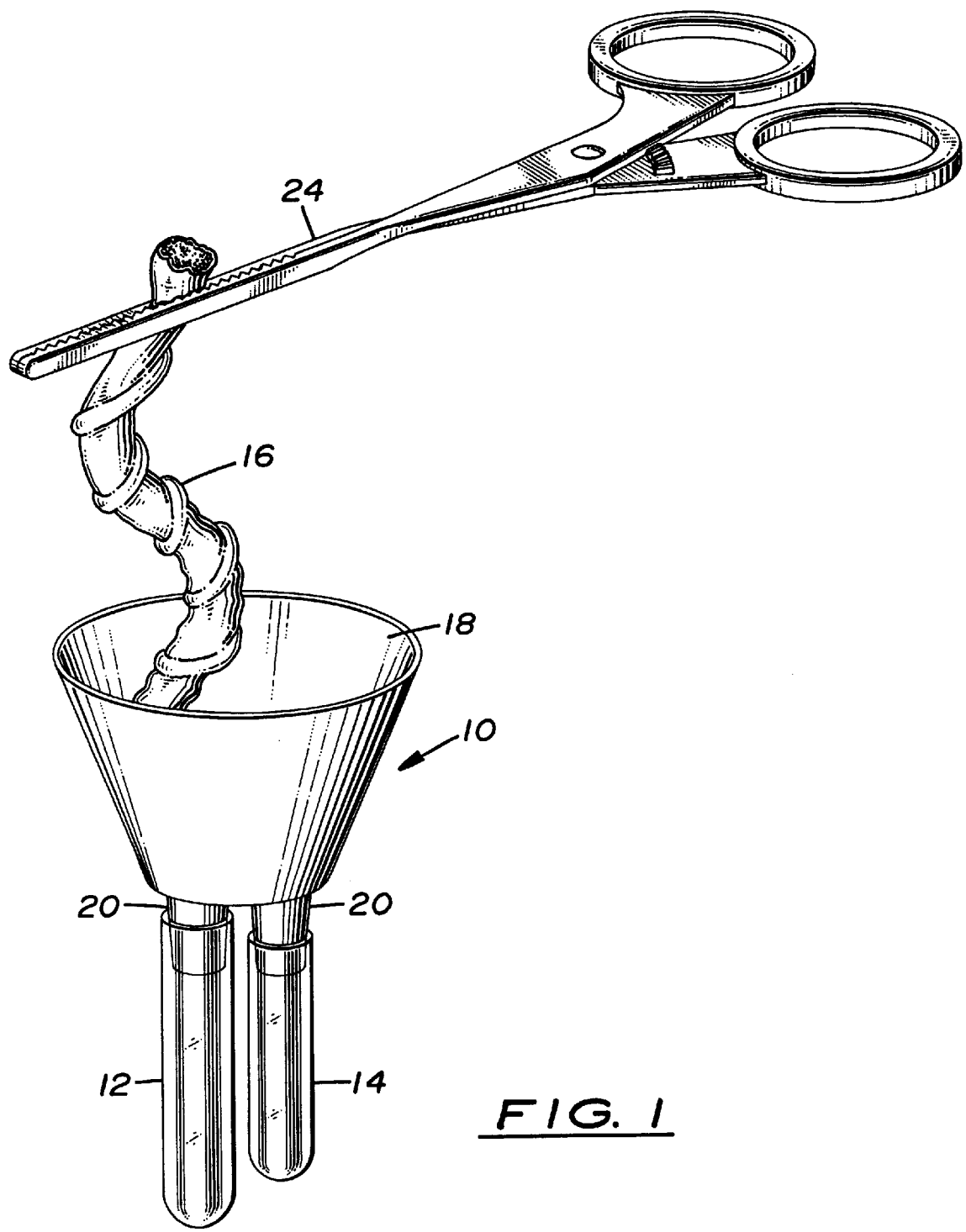
FIG. 1 is an environmental perspective of a blood collection funnel according to the present invention with two test tubes attached to the funnel.

The present invention is to a system and method for collecting blood during delivery procedures using a blood collection funnel 10 and a plurality of test tubes 12,14.

As best shown in FIG. 1, a blood collection funnel 10 is provided for collecting blood (not shown) from an umbilical cord 16 of a newborn infant (not shown). Immediately after birth, blood must be collected from the newborn to determine the blood type, RH factor and blood count of the newborn. In addition, other tests such as the additional bilirubin present in the cord must be performed. If the doctor is concerned about particular problems such as drug use by the parent or diseases such as AIDS which may affect the newborn based on the parental history of the newborn, then other blood tests may also have to be performed.

In contrast to earlier practiced methods of collecting blood from newborns such as holding the umbilical cord over a medicine glass or using a syringe to draw blood from the cord or the placenta, the present method offers a simpler and more effective way of collecting blood. The blood collection funnel offers a wide mouth 18 at an upper end of a receiving chamber for receiving flow and a plurality of spouts 20 for directing flow out of the funnel. The tapered edges of the funnel direct flow from the mouth 18 to the spouts 20. As shown best in FIG. 2, the funnel may have a flat of less sloped area to the funnel near the tops of the spouts 12,14 to help distribute the blood to the test tubes. Obviously one skilled in the art would recognize that the shape of the funnel could be altered to help proportion the flow to the funnels, or the spouts could be of different or the same sizes to accept test tubes of different sizes or similar size openings. One skilled in the art would also appreciate that more than two spouts could be provided to distribute blood to more than two test tubes. One would also appreciate that clamps or other devices could be used to stem the flow of blood from the funnel to the test tubes to prevent spillage when the test tubes are full.

In practice, as best shown in FIGS. 1–4, in preparation for collecting blood from the umbilical cord of a newborn, a nurse or other medical personnel collects two test tubes (FIG. 4), removes the color coordinated caps from the tubes. The proper chemicals for preparation and preservation of the blood samples may be pre-poured into the tubes or chemicals can be added to the tubes in preparation for receiving the blood. Obviously, one or more of the tubes can have no chemicals in the tube to preserve the purity of the blood, if later tests so require.

Once the test tubes have been prepared the upper end of the test tubes 12,14 are inserted over the appropriate spout 20 at the lower end of the funnel as shown progressively in FIGS. 3 and 1. One the test tubes are secured in place about the lower spouts of the funnel by frictional interference fit or held in place by other means, the funnel and attached tubes are set to receive blood.

The doctor or other personnel clamps the umbilical cord in the proper place using well known clamps 24 and cuts a section of the umbilical cord from the rest of the cord. The clamped umbilical cord is then held over the funnel as shown in FIG. 1 and an end of the umbilical cord is unclamped allowing blood to free flow into the funnel. When the proper amount of blood is released into the funnel, the umbilical cord is then reclamped, if necessary, to prevent further blood from entering the funnel. As soon as the blood as drained from the funnel into the blood collection tubes, the tubes may be removed and capped. The caps 26,28 may be color coded to signify blood samples which should be directed to certain lab or lab test, or may signify the presence or absence of added chemicals such as anticoagulants or other agents added to preserve or prepare the blood sample for further tests. This is important as it is standard practice to send the blood off to two separate labs, one for blood typing and counting, and the other for other various work ups.

The blood collection funnel 10 can then be disposed of or sent to cleaning and sterilization depending on the material composition of the funnel. It is anticipated that a plastic material is best suited for use as a disposable blood collection funnel to limit the possibility of blood contamination and simplify use of the equipment.

The use of the blood collection funnel decreases the likelihood of spillage by providing the large opening 18 at the top of the funnel 10, thus lowering the likelihood of blood contamination or exposure to spilled and uncontained blood. The directional spouts 20 allow blood to be directed into test tubes 12,14 which can have chemicals before the blood is received in the funnel, or may chemicals added prior to capping of the test tubes. The tubes being free from blood or other contamination can capped and sent directly to the appropriate lab or sent to different labs. Color coordinated caps on the test tubes can be used to signify the contents of the tube and the appropriate destination or test for the blood sample.

The increased likelihood of successful receiving blood from the umbilical cord into the test tubes allows the blood to be sealed or mixed with anticoagulant agents to preserve and protect the blood samples. By increasing the success rate of preserving useable blood samples, the chances of having to collect blood by other means is lessened. Therefore, the probability of having to collect blood using a syringe from the cord, from the placenta, or from the newborn is reduced, saving money, time, and the possibility of exposure to potentially dangerous blood filled syringes.

It is to be understood that the present invention is not limited to the sole embodiment described above, but encompasses any and all embodiments within the scope of the following claims.

I claim:

1. A kit for collecting blood consisting of:
   a) a unitary funnel having a central tapered chamber communicating with two test tube receiving spouts;
   b) said two test tube receiving spouts each being tapered to securely receive and maintain a respective test tube in communication therewith by interference fit;
   c) a pair of test tubes sized to be received on said two test tube receiving spouts for receiving blood therein from said funnel;
   whereby blood from an umbilical cord of a newborn baby can be poured into said funnel to simultaneously fill said pair of test tubes for storage and transportation to testing facilities.

2. The kit for collecting blood of claim 1, wherein a first test tube of said plurality of test tubes is larger than a second test tube of said plurality of test tubes.

3. A kit for collecting blood and simultaneously separating the blood into multiple test tubes comprising:

a) a funnel having a central tapered chamber and a plurality of spouts in fluid communication with said chamber;

b) at least one of said plurality of spouts being tapered to securely receive and maintain a respective test tube in communication therewith by interference fit;

c) a plurality of test tubes sized to be secured on said plurality of spouts;

whereby said test tubes can be slid onto said spouts and held in place by interference fit, while the umbilical cord of a newborn baby is placed within said funnel and blood from the cord can be simultaneously transferred to said plurality of test tubes, and said test tubes can be remove for transportation of the blood.

4. The kit according to claim 3, wherein at least one of said plurality of test tubes is larger than at least one other of said plurality of test tubes.

5. A method of collecting blood during childbirth from an umbilical cord comprising the steps of:

a) providing a plurality of test tubes;

b) providing a funnel having an upper receiving chamber and a plurality of lower directing spouts simultaneously in fluid communication with said receiving chamber;

c) providing each of said plurality of directing spouts with a tapered outer wall sized to provide an interference fit with an inner wall of a respective one of said plurality of test tubes;

d) inserting at least two of said plurality of spouts respectively into at least two of said plurality of test tubes;

e) placing an umbilical cord from a newborn over said funnel and pouring the blood over said funnel;

f) at least partially filling said at least two of said plurality of test tubes with blood; and g) removing at least one of said at least two of said plurality of test tubes filled with blood.

6. The method of collecting blood according to claim 5, wherein said source of blood is a clamped section of umbilical cord from a newborn infant.

7. The method of collecting blood according to claim 5, further comprising the step of added a blood preparation chemical to at least one of said plurality of test tubes prior to step inserting at least one of said plurality of spouts into at least one of said plurality of test tubes.

8. The method of collecting blood according to claim 5, further comprising the steps of:

f) removing at least one of said plurality of test tubes from said funnel; and g) capping said removed at least one test tube; and h) marking at least one of said removed at least one test tube with an identifying signal.

9. The method of collecting blood according to claim 8, wherein said identifying signal is a color coded cap.

10. The method of collecting blood according to claim 8, further comprising the steps of:

i) sending said removed at least one test tube to testing; and j) disposing of said funnel.

11. The method of collecting blood according to claim 8, further wherein said provided funnel has two spouts.

* * * * *